US012618825B2

(12) United States Patent
Pajouhi et al.

(10) Patent No.: US 12,618,825 B2
(45) Date of Patent: May 5, 2026

(54) BIOLOGICAL SENSING SYSTEM HAVING MICRO-ELECTRODE ARRAY

(71) Applicant: Purdue Research Foundation, West Lafayette, IN (US)

(72) Inventors: Hossein Pajouhi, West Lafayette, IN (US); Saeed Mohammadi, Zionsville, IN (US); Mojgan Sarmadi, Zionsville, IN (US)

(73) Assignee: Purdue Research Foundation, West Lafayette, IN (US)

( * ) Notice: Subject to any disclaimer, the term of this patent is extended or adjusted under 35 U.S.C. 154(b) by 263 days.

(21) Appl. No.: 18/134,890

(22) Filed: Apr. 14, 2023

(65) Prior Publication Data

US 2023/0400450 A1     Dec. 14, 2023

Related U.S. Application Data

(62) Division of application No. 15/815,700, filed on Nov. 16, 2017, now abandoned.

(Continued)

(51) Int. Cl.
*H01L 23/528* (2006.01)
*G01N 33/483* (2006.01)
(Continued)

(52) U.S. Cl.
CPC ... *G01N 33/4836* (2013.01); *H01L 21/32135* (2013.01); *H01L 21/32139* (2013.01); *H01L 21/76834* (2013.01); *H01L 23/5283* (2013.01); *H01L 23/66* (2013.01); *H10D 86/01* (2025.01); *H10D 86/201* (2025.01);
(Continued)

(58) Field of Classification Search
CPC .......... G01N 33/4836; H01L 21/32135; H01L 21/32139; H01L 21/76834; H01L 23/5283; H01L 23/66; H01L 23/53228; H01L 2221/1094; H01L 2223/6677; H10D 86/01; H10D 86/201; H10D 86/441; H10D 86/60
See application file for complete search history.

(56) References Cited

U.S. PATENT DOCUMENTS 5,847,454 A * 12/1998 Shaw .................... B81C 1/0015
257/734
6,455,931 B1 * 9/2002 Hamilton, Jr. ........ H01F 39/011
257/723

(Continued)

OTHER PUBLICATIONS

V. Marx, Nat. Methods 11, 1099 (2014).
(Continued)

*Primary Examiner* — Binh X Tran
*Assistant Examiner* — Christopher Remavege
(74) *Attorney, Agent, or Firm* — Purdue Research Foundation

(57)                    ABSTRACT

A biological sensing system, comprising a microelectrode array having a plurality of islands that are thermally isolated from each other and are interconnected by flexible nano-scale wires. An embedded complementary metal oxide semiconductor (CMOS) instrumentation amplifier and wireless communication circuitry may be operatively connected to the microelectrode array and embedded within input/output pads connected to the wires at the periphery of the array.

4 Claims, 26 Drawing Sheets

Related U.S. Application Data

(60) Provisional application No. 62/423,199, filed on Nov. 16, 2016.

(51) Int. Cl.

| | |
|---|---|
| *H01L 21/3213* | (2006.01) |
| *H01L 21/768* | (2006.01) |
| *H01L 23/532* | (2006.01) |
| *H01L 23/66* | (2006.01) |
| *H10D 86/00* | (2025.01) |
| *H10D 86/01* | (2025.01) |
| *H10D 86/40* | (2025.01) |
| *H10D 86/60* | (2025.01) |

(52) U.S. Cl.
CPC ........... *H10D 86/441* (2025.01); *H10D 86/60* (2025.01); *H01L 23/53228* (2013.01); *H01L 2221/1094* (2013.01); *H01L 2223/6677* (2013.01)

(56) References Cited

U.S. PATENT DOCUMENTS

| | | | | |
|---|---|---|---|---|
| 6,712,983 | B2 * | 3/2004 | Zhao | B81C 1/00571 |
| | | | | 216/2 |
| 7,084,028 | B2 * | 8/2006 | Fukuzumi | H10B 12/09 |
| | | | | 438/57 |
| 8,371,167 | B2 * | 2/2013 | Wang | G01P 15/125 |
| | | | | 73/514.32 |
| 8,440,546 | B2 * | 5/2013 | Nuzzo | H10D 62/121 |
| | | | | 438/106 |
| 8,886,334 | B2 | 11/2014 | Ghaffari et al. | |
| 9,119,533 | B2 * | 9/2015 | Ghaffari | H10F 39/016 |
| 9,224,629 | B2 * | 12/2015 | Golda | H02N 13/00 |
| 9,352,959 | B1 * | 5/2016 | Bulovic | H01S 5/187 |
| 9,437,628 | B1 * | 9/2016 | Ma | G01N 22/00 |
| 9,450,043 | B2 * | 9/2016 | Nuzzo | H01L 24/97 |
| 10,292,261 | B2 * | 5/2019 | Rogers | H01L 21/4867 |
| 10,334,724 | B2 * | 6/2019 | Hsu | H05K 1/0283 |
| 11,271,179 | B2 * | 3/2022 | Kim | H10K 77/111 |
| 2002/0094701 | A1 * | 7/2002 | Biegelsen | B25J 13/084 |
| | | | | 439/32 |
| 2008/0173971 | A1 | 7/2008 | Sharma et al. | |
| 2008/0318030 | A1 * | 12/2008 | Handy | H01L 21/6835 |
| | | | | 428/354 |
| 2009/0255801 | A1 | 10/2009 | Haas | |
| 2009/0283891 | A1 * | 11/2009 | Dekker | H05K 1/0283 |
| | | | | 257/E23.177 |
| 2010/0002402 | A1 * | 1/2010 | Rogers | H01L 23/4985 |
| | | | | 361/749 |
| 2010/0143848 | A1 * | 6/2010 | Jain | B23K 26/40 |
| | | | | 430/311 |
| 2010/0178722 | A1 * | 7/2010 | de Graff | H01L 21/30 |
| | | | | 438/73 |
| 2011/0000060 | A1 * | 1/2011 | Lee | H10N 39/00 |
| | | | | 29/25.35 |
| 2011/0054583 | A1 | 3/2011 | Litt et al. | |
| 2011/0084356 | A1 * | 4/2011 | Saarnilehto | H01L 21/76283 |
| | | | | 257/E29.02 |
| 2011/0208029 | A1 | 8/2011 | Joucla et al. | |
| 2012/0157804 | A1 * | 6/2012 | Rogers | A61B 5/076 |
| | | | | 604/20 |
| 2012/0165759 | A1 * | 6/2012 | Rogers | H05K 1/0283 |
| | | | | 606/228 |
| 2012/0261551 | A1 * | 10/2012 | Rogers | G02B 26/0825 |
| | | | | 359/619 |
| 2013/0041235 | A1 * | 2/2013 | Rogers | A61B 5/282 |
| | | | | 600/386 |
| 2013/0316487 | A1 * | 11/2013 | de Graff | H10F 39/011 |
| | | | | 438/66 |
| 2013/0333094 | A1 * | 12/2013 | Rogers | A61B 5/6806 |
| | | | | 340/407.1 |
| 2014/0233614 | A1 * | 8/2014 | Crawley | H04B 1/40 |
| | | | | 375/219 |
| 2014/0303452 | A1 * | 10/2014 | Ghaffari | A61B 18/20 |
| | | | | 601/3 |
| 2014/0340857 | A1 | 11/2014 | Hsu et al. | |
| 2015/0287607 | A1 * | 10/2015 | Xu | H01L 21/3065 |
| | | | | 438/126 |
| 2015/0380355 | A1 * | 12/2015 | Rogers | H01L 23/5387 |
| | | | | 257/773 |
| 2016/0005700 | A1 * | 1/2016 | Rogers | H01L 21/28 |
| | | | | 438/107 |
| 2017/0049612 | A1 * | 2/2017 | Hussain | A61F 7/007 |
| 2017/0338453 | A1 * | 11/2017 | Yu | H01L 21/561 |
| 2018/0263539 | A1 * | 9/2018 | Javey | A61B 5/1477 |

OTHER PUBLICATIONS

X. Duan, T. M. Fu, J. Liu, and C. M. Lieber, Nano Today 8, 351 (2013).

N. A. Kouklin, W. E. Kim, A. D. Lazareck, and J. M. Xu, Appl. Phys. Lett. 87, 173901 (2005).

C. Nick, S. Yadav, R. Joshi, J. J. Schneider, and C. Thielemann, Appl. Phys. Lett. 107, 013101 (2015).

Q. Qing, Z. Jiang, L. Xu, R. Gao, L. Mai, and C. M. Lieber, Nat. Nanotechnol. 9, 142 (2014).

S. Meyburg, G. Wrobel, R. Stockmann, J. Moers, S. Ingebrandt, and A. Offenhausser, Appl. Phys. Lett. 89, 013901 (2006).

J. Müller, M. Ballini, P. Livi, Y. Chen, M. Radivojevic, A. Shadmani, V. Viswam, I. L. Jones, M. Fiscella, R. Diggelmann, A. Stettler, U. Frey, D.J. Bakkum, and A. Hierlemann, Lab Chip 15, 2767 (2015).

J. T. Robinson, M. Jorgolli, A. K. Shalek, M.-H. Yoon, R. S. Gertner, and H. Park, Nat. Nanotechnol. 7, 180 (2012).

T. Datta-Chaudhuri, P. Abshire, and E. Smela, Lab Chip 14, 1753 (2014).

J. Viventi, D. H. Kim, L. Vigeland, E. S. Frechette, J. A. Blanco, Y. S. Kim, A. E. Avrin, V. R. Tiruvadi, S. W. Hwang, A. C. Vanleer, D. F. Wulsin, K. Davis, C. E. Gelber, L. Palmer, J. Van der Spiegel, J. Wu, J. Xiao, Y. Huang, D. Contreras, J. A. Rogers, and B. Litt, Nat. Neurosci. 14, 1599 (2011).

D. H. Kim, N. Lu, R. Ghaffari, Y. S. Kim, S. P. Lee, L. Xu, J. Wu, R. H. Kim, J. Song, Z. Liu, J. Viventi, B. de Graff, B. Elolampi, M. Mansour, M.J. Slepian, S. Hwang, J. D. Moss, S. M. Won, Y. Huang, B. Litt, and J. A. Rogers, Nat. Mater. 10, 316 (2011).

D. H. Kim, N. Lu, R. Ma, Y. S. Kim, R. H. Kim, S. Wang, J. Wu, S. M. Won, H. Tao, A. Islam, K. J. Yu, T. Kim, R. Chowdhury, M. Ying, L. Xu, M. Li, H. J. Chung, H. Keum, M. McCormick, P. Liu, Y. W. Zhang, F. G. Omenetto, Y. Huang, T. Coleman, and J. A. Rogers, Science (80-.) 333, 838 (2011).

D. Shahrjerdi and S. W. Bedell, Nano Lett. 13, 315 (2013).

W. Peng, M. M. Roberts, E. P. Nordberg, F. S. Flack, P. E. Colavita, R. J. Hamers, D. E. Savage, M. G. Lagally, and M. A. Eriksson, Appl. Phys. Lett. 90, 183107 (2007).

D. H. Kim, S. Wang, H. Keum, R. Ghaffari, Y. S. Kim, H. Tao, B. Panilaitis, M. Li, Z. Kang, F. Omenetto, Y. Huang, and J. A. Rogers, Small 8, 3263 (2012).

S. Mack, M. A. Meitl, A. J. Baca, Z. T. Zhu, and J. A. Rogers, Appl. Phys. Lett. 88, 213101 (2006).

Y. Xu, IEEE Sens. J. 13, 3962 (2013).

N. Inomata, M. Toda, M. Sato, A. Ishijima, and T. Ono, Appl. Phys. Lett. 100, 154104 (2012).

K. Okabe, N. Inada, C. Gota, Y. Harada, T. Funatsu, and S. Uchiyama, Nat. Commun. 3, 705 (2012).

H. Xie, S. Member, L. Erdmann, and X. Zhu, J. Microelectromech. Syst. 11, 93 (2002).

J. L. Muñoz-Gamarra, A. Uranga, and N. Barniol, Appl. Phys. Lett. 104, 243105 (2014).

H. Fu, S. Xu, R. Xu, J. Jiang, Y. Zhang, J. A. Rogers, and Y. Huang, Appl. Phys. Lett. 106, 091902 (2015).

H. C. Ko, G. Shin, S. Wang, M. P. Stoykovich, J. W. Lee, D.-H. Kim, J. S. Ha, Y. Huang, K-C. Hwang, and J. A. Rogers, Small 5, 2703 (2009).

B. D. Chan, K. Icoz, W. Huang, C.-L. Chang, and C. A. Savran, Lab Chip 14, 4188 (2014).

(56)          References Cited

OTHER PUBLICATIONS

B. D. Chan, F. Mateen, C. L. Chang, K. Icoz, and C. A. Savran, J. Microelectromechanical Sytems 21, 2011 (2012).
J. Christofferson and A. Shakouri, Rev. Sci. Instrum. 76, 024903 (2005).
H. Pajouhi, A. Y. Jou, R. Jain, A. Ziabari, A. Shakouri, C. A. Savran, and S. Mohammadi, Flexible complementary metal oxide semiconductor microelectrode arrays with applications in single cell characterization, Applied Physics etters, 107, 203103, (2015).

* cited by examiner

Aluminum

Oxide

Silicon

Aluminum

Oxide

Silicon (d)

PDMS curvature

BIOLOGICAL SENSING SYSTEM HAVING MICRO-ELECTRODE ARRAY

CROSS-REFERENCE TO RELATED APPLICATIONS

The present patent application is a divisional of U.S. patent application Ser. No. 15/815,700 filed Nov. 16, 2017, which is related to and claims the priority benefit of U.S. Provisional Patent Application Ser. No. 62/423,199, filed Nov. 16, 2016, the contents of which are hereby incorporated by reference in their entireties into the present disclosure.

TECHNICAL FIELD

The present disclosure generally relates to biological sensors, and in particular to a biological sensing system having a microelectrode array.

BACKGROUND

This section introduces aspects that may help facilitate a better understanding of the disclosure. Accordingly, these statements are to be read in this light and are not to be understood as admissions about what is or is not prior art.

Biological sensing at micro- and nano-scales facilitated by high performance electrodes leads to a better understanding of single cell behavior. A variety of such electrodes have been developed to record electrical activities of beating cells, using both intracellular and extracellular techniques. A planar high-density microelectrode array (MEA) is an example of such electrodes utilized in an extracellular in-vitro measurement for interfacing to neurons. Moreover, nanoscopic probes, such as nanopillar electrode arrays, are extensively used for intracellular action potential measurement of individual neurons. The weak nature of biological signals combined with three-dimensional moving surfaces of cells and tissues demand tight integration of an array of flexible electrodes with electronic amplifier circuits to enhance the recovery of such signals. While novel flexible electronic sensors with improved sensitivities have been developed, they still require a number of leads coming out of the sensor array and in some cases require external instrumentation amplifiers for signal recovery. Such designs not only lead to loss of the overall sensitivity and reduced measurement bandwidth but also demand complex integration and packaging approaches. At the cellular level, three-dimensional kinked nanowire FETs have been proposed for single cell action potential recording. The kinked nanowire based designs have achieved high sensitivity at the sensor level, but require external amplifiers with associated path loss and undesired coupling, compromising their overall sensitivity. At the tissue level, three-dimensional flexible circuits on deformable sheets that bend according to the curvatures of tissues, provide interface for in-vivo characterization. While these techniques have utilized simple integrated electronics, they can benefit from large scale integration in order to reduce the distance among array sensors, further reducing the number of leads coming out of the array (analog multiplexing) and enhancing detected signals achieved by analog and digital signal processing and amplification.

Prior art flexible electronic circuits are typically based on either thinned-down Si flakes that can only bend at a few millimeter radius to prevent damage or transferred-printed silicon micro-islands, presumably characterized with low yield as device density increases. Therefore, improvements are needed in the field.

BRIEF DESCRIPTION OF THE DRAWINGS

FIG. 5(d) is without lock-in amplifier in 1 degree C. steps and FIG. 5(e) is with the integrated CMOS lock-in amplifier in 0.1 degree C. steps.

DETAILED DESCRIPTION

Figure 1A:
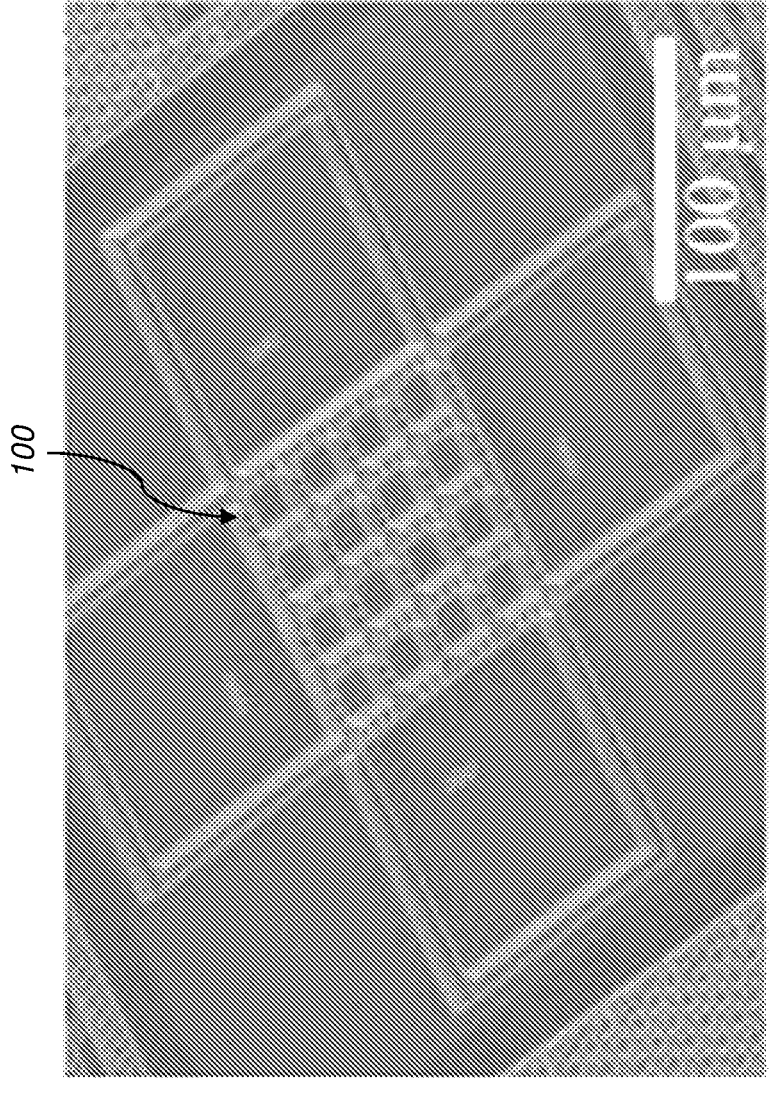
FIG. 1(a) shows the SEM images of a microarray structure on a CMOS SOI chip.
Figure 1B:
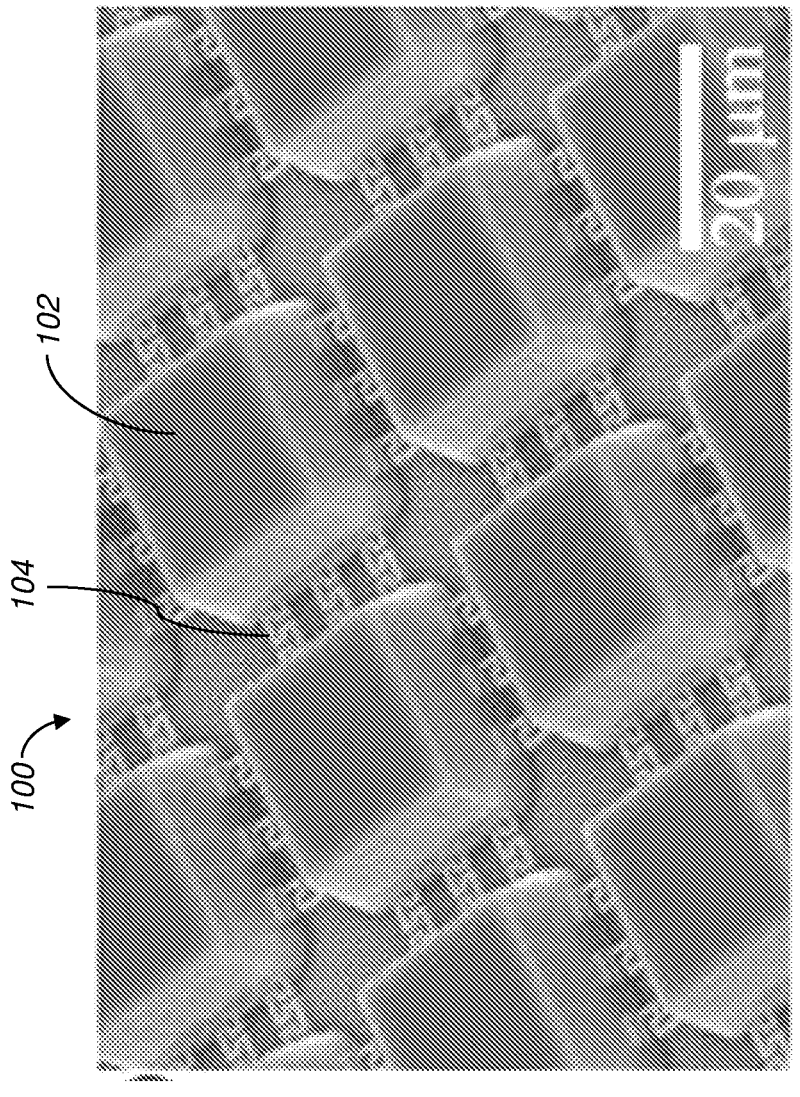
FIG. 1(b) shows microarray islands after a plasma etch and before release.
Figure 1C:
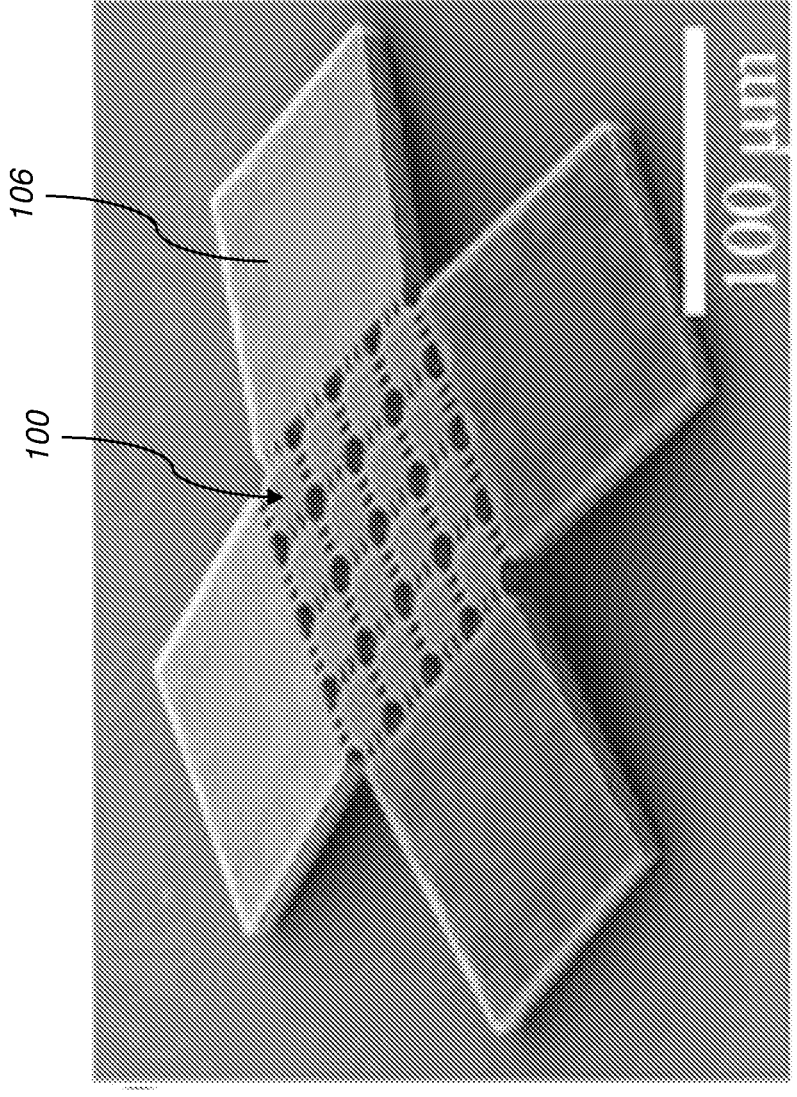
FIG. 1(c) shows a released microelectrode array.
Figure 1D:
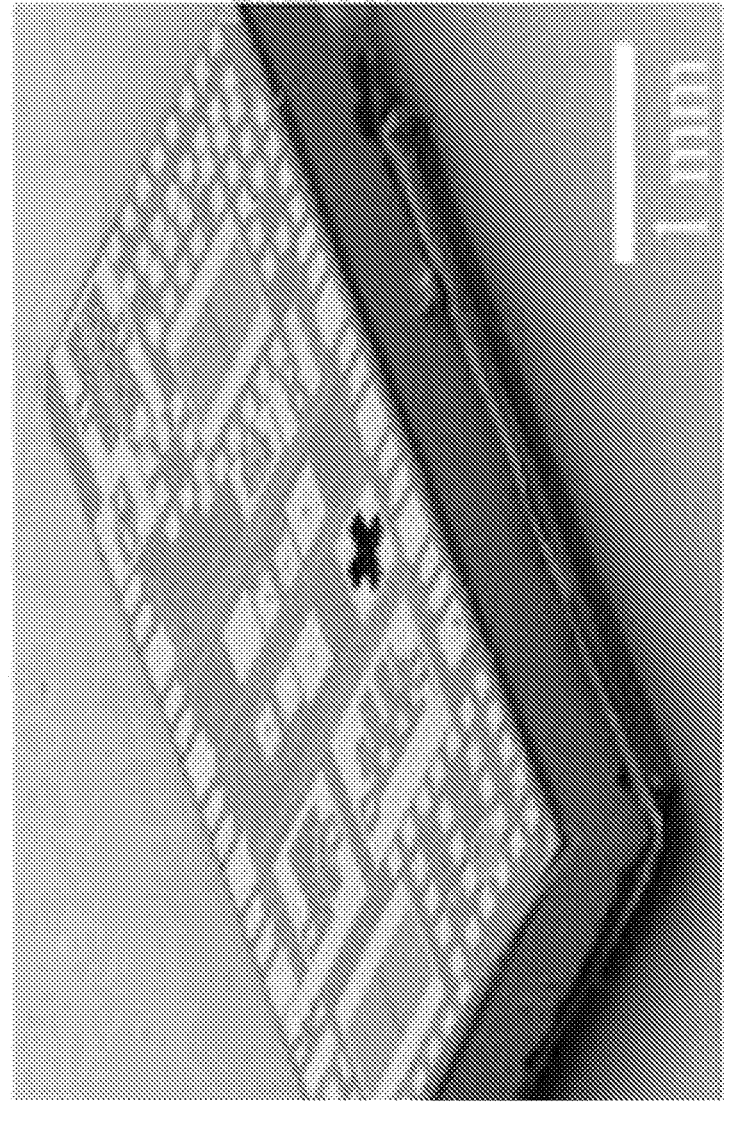
FIG. 1(d) shows the chip after the release of the microelectrode array.
Figure 2A:
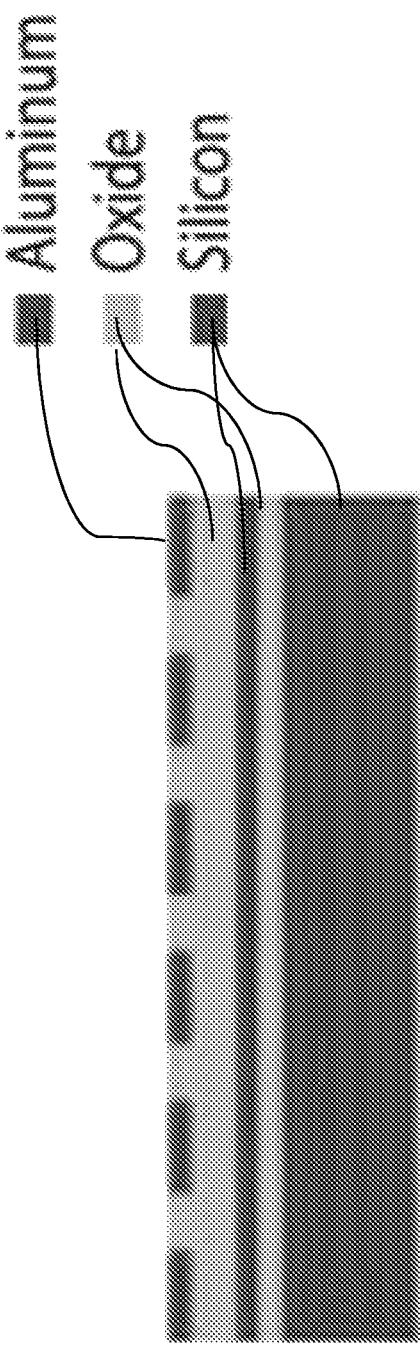
FIG. 2(a) shows a CMOS chip after fabrication in a foundry according to one embodiment.
Figure 2B:
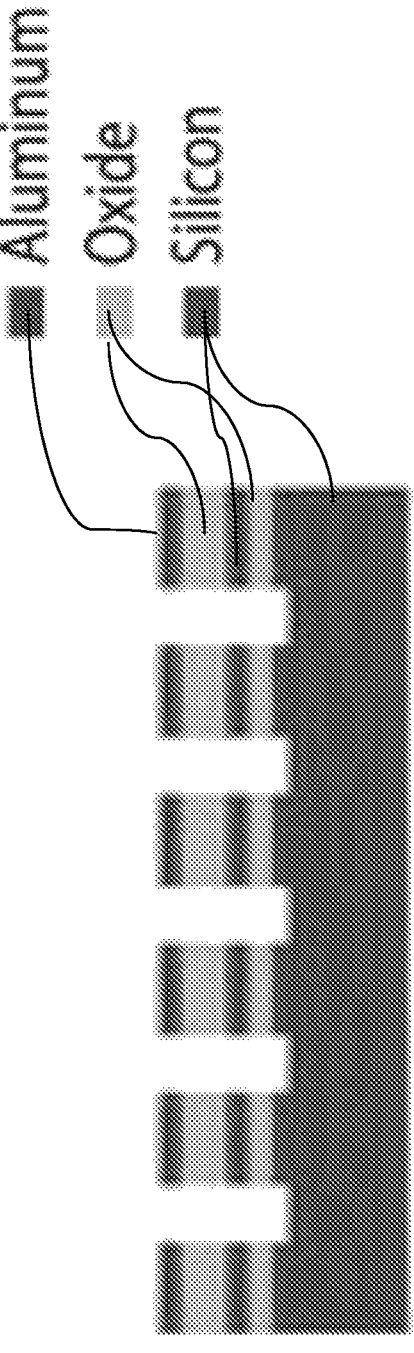
FIG. 2(b) shows anisotropic dry etching using ICP.
Figure 2C:
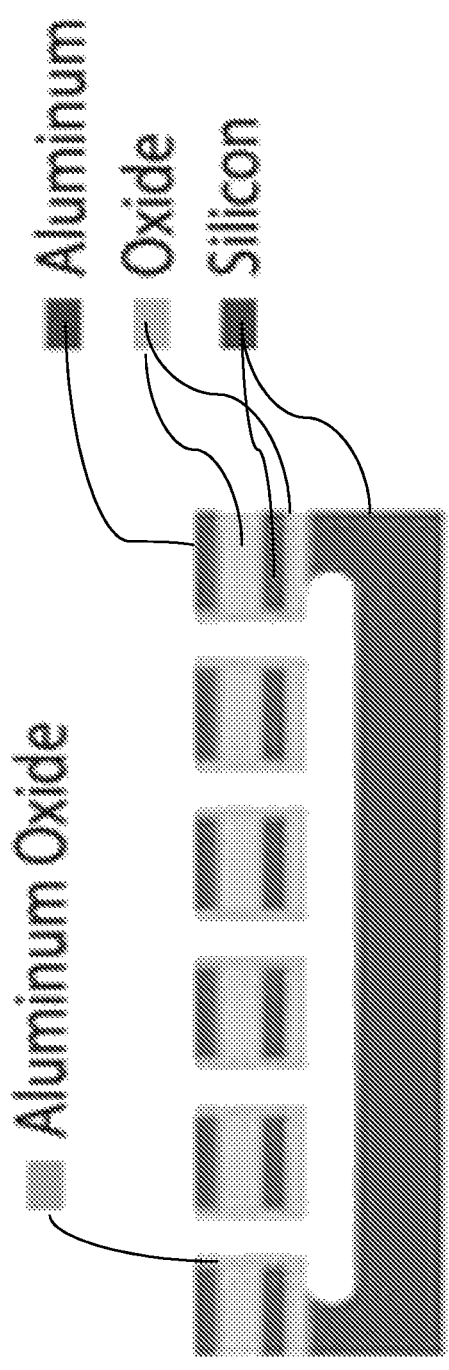
FIG. 2(c) shows aluminum oxide deposition followed by ICP anisotropic etching and XeF2 isotropic etching. The SOI Oxide layer (buried oxide) served as intrinsic etch-stop to protect the island from the bottom.
Figure 2D:
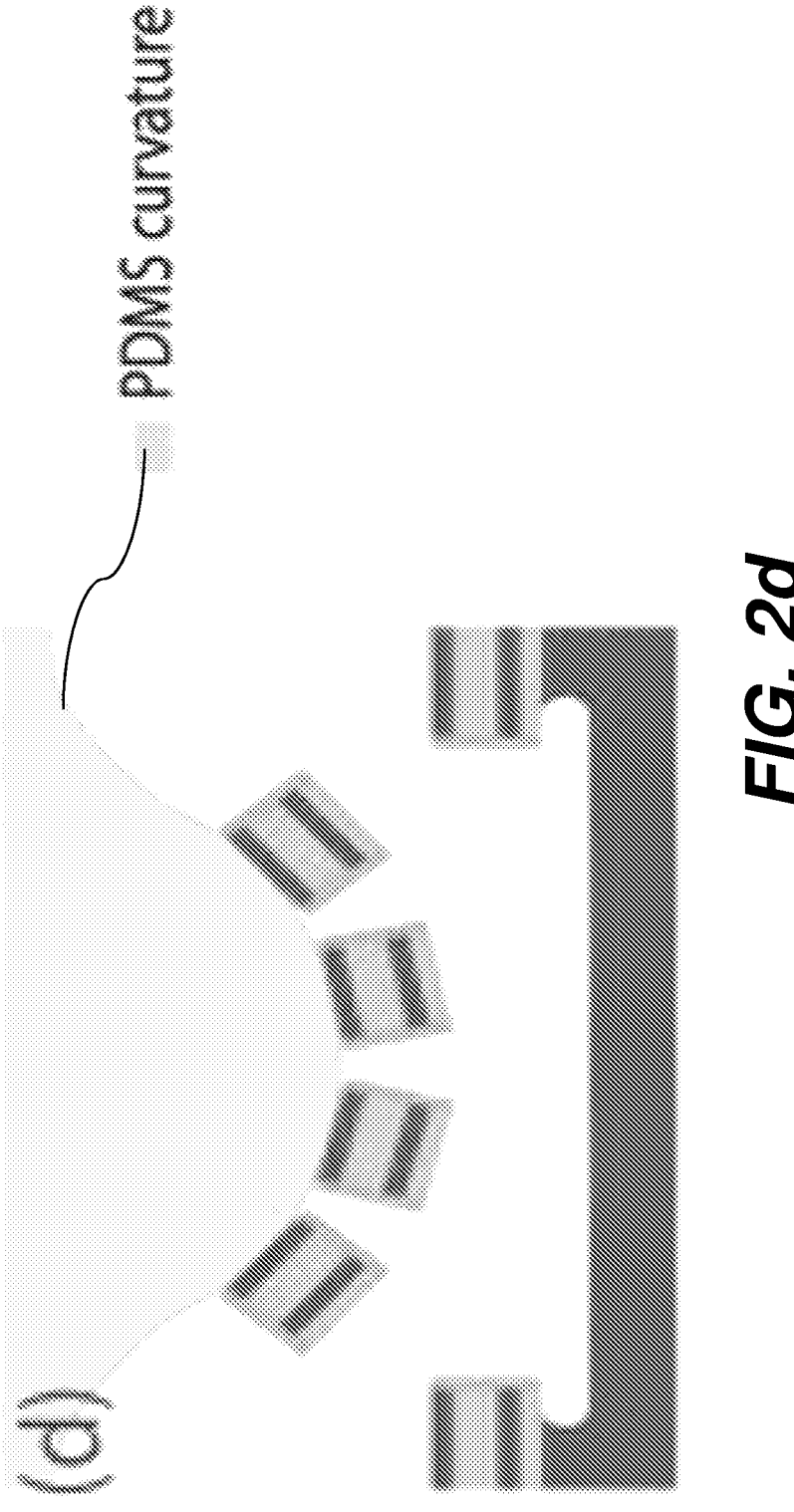
FIG. 2(d) shows transfer of the array using a PDMS transfer-printing technique.
Figure 2E:
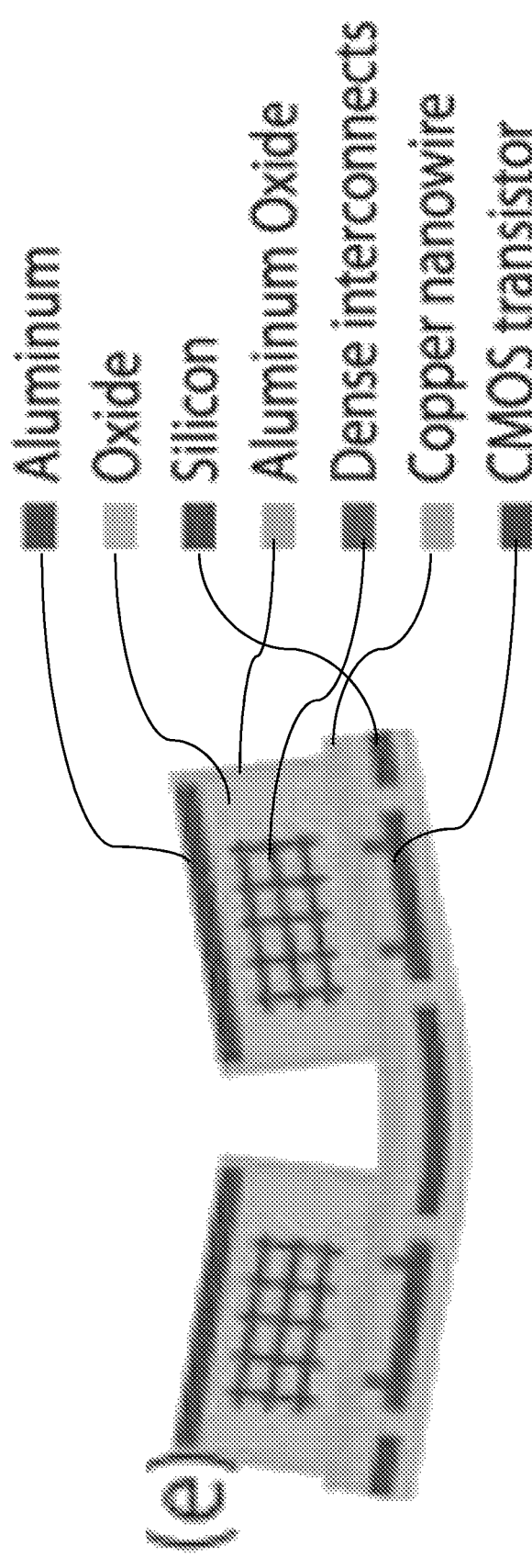
FIG. 2(e) shows a zoomed-in schematic of two cells of the array and the nanowire interconnects.
Figure 3A:
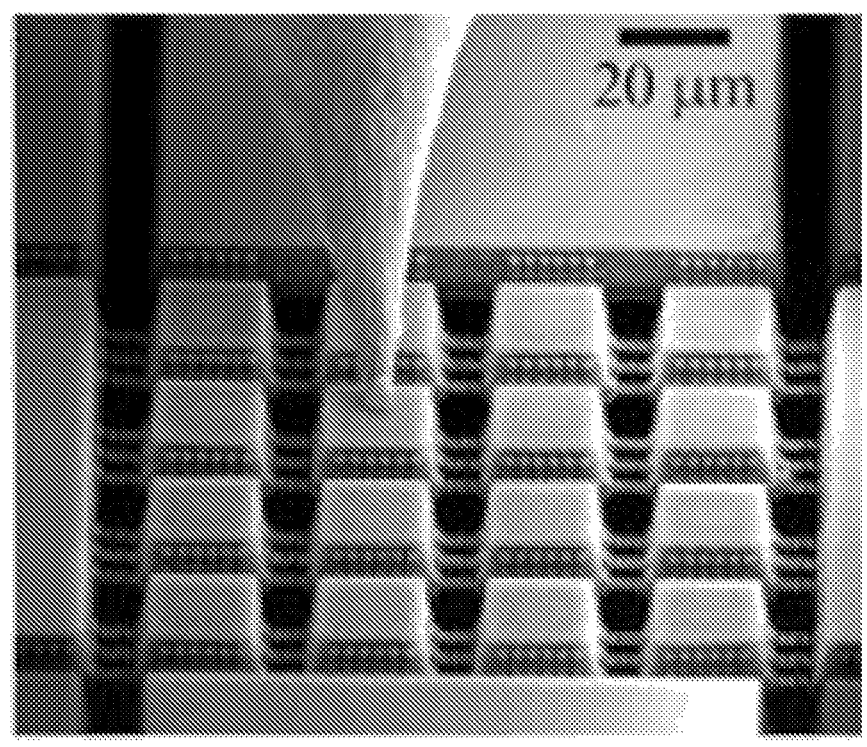
FIG. 3(a) shows a SEM micrograph illustrates the microelectrode array inside the FIB vacuum chamber. The tip is located on the surface of a micro island.
Figure 3B:
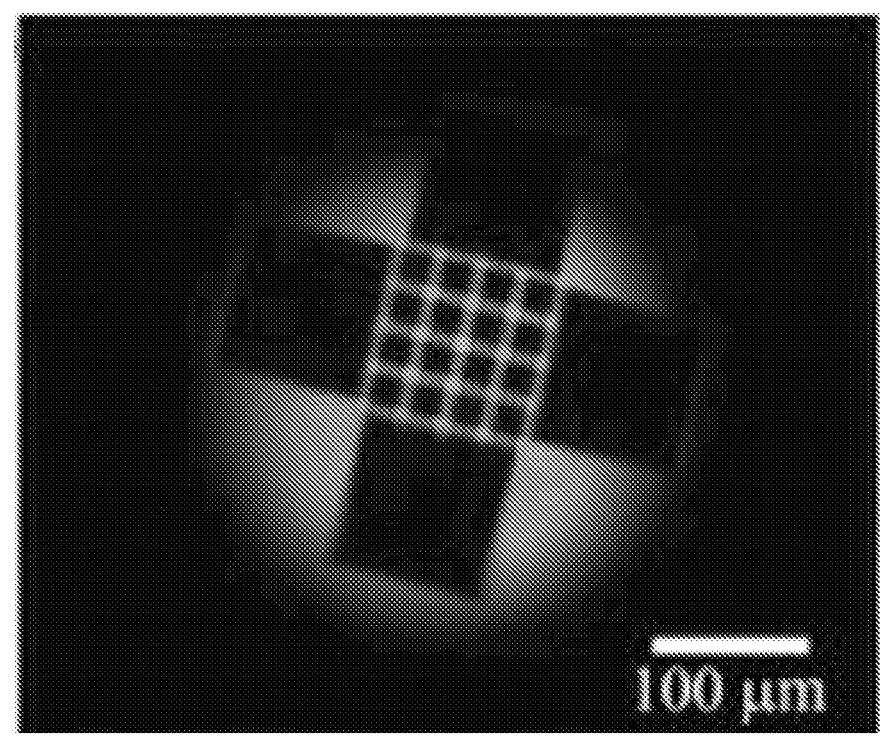
FIG. 3 (b) shows a fluorescent microscope image of the array laminating on a 220 lm fluorescent micro-bead.
FIG. 3(c) shows a SEM image which illustrates the bent array under the Nanorobotic tip force.
FIG. 3(d) shows a false color SEM image of the microelectrode array transfer-printed on a florescent microsphere. Inset illustrates false color SEM image of the microelectrode array transfer-printed on a florescent microsphere.
Figure 3C:
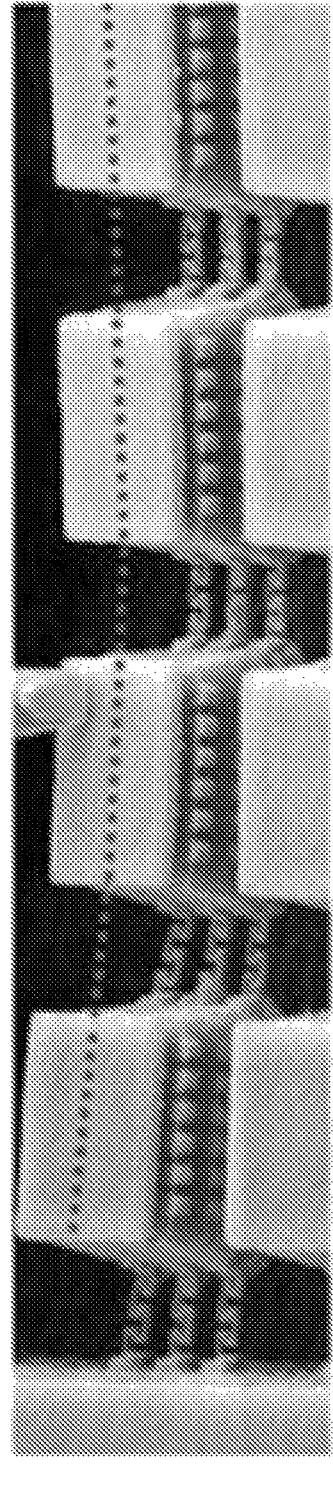
Figure 3D:
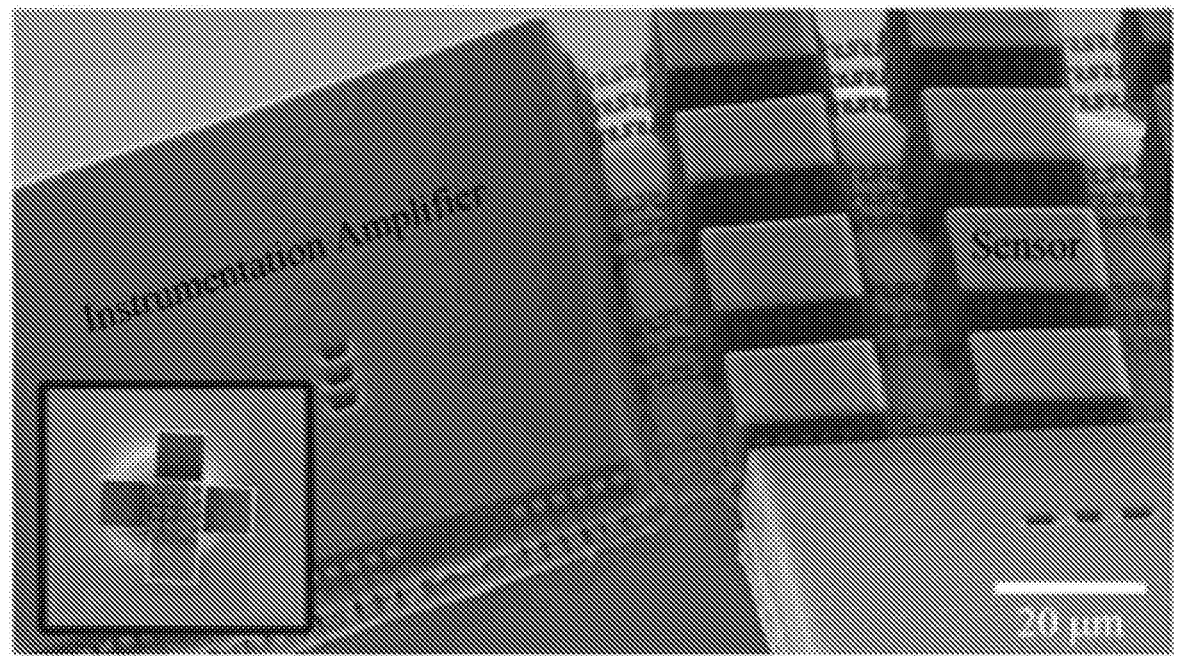

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In response to the unmet need, disclosed herein is an ultra-flexible microelectrode array based on complementary metal oxide semiconductor (CMOS) ultrathin membranes. The array can be easily laminated on micron-size curved surfaces such as the surface of a single biological cell, and is equipped with very dense electronics. To demonstrate the functionality of complex electronics on the array, CMOS temperature sensors and instrumentation amplifiers for precision single cell thermometry are implemented and tested. The operating conditions of CMOS transistors utilized as temperature sensors are optimized to enhance the measurement sensitivity.

Cell temperature is an indicator of cellular processes such as cell division, metabolism, and enzyme reaction. For example, precision cell thermometry can identify cancer cells that are characterized with slightly higher temperatures than normal cells. Additionally, the temperature across a single cell is not constant and is slightly elevated around mitochondrion due to their high metabolism. While accurate in-vivo measurement of temperature across a cell is important, understanding the behavior of a cell demands other sensors such as potential and pH sensors to be integrated within the flexible sensing platform. Such a flexible microelectrode array with integrated sensors and electronic amplifiers is an instrumental tool for understanding the cell behavior without disturbing its environment.

A CMOS technology (Global Foundries 45 nm Silicon on Isolator) that brings about reliability, reproducibility and large integration capability at low development costs is utilized in the present disclosure. Arrays 100 of a plurality (e.g., 4×4 as shown in FIGS. 1(*a*) and 1(*b*)) ultrathin CMOS islands 102 interconnected by meandered copper (Cu) metal nano-scale wires 104 are transfer-printed in one piece onto host substrates or cells, bypassing the yield-limiting obstacles of previously reported transfer-printing techniques for complex circuits. As shown in the example of FIGS. 1(*a*) and 1(*b*), each island 102 of the array 100 is 19×19 $\mu$m$^2$ with a thickness of about 10 $\mu$m (A stack of 220 nm Silicon on Insulator (SOI) layer and a rv10 $\mu$m thick interconnection/ oxide layer on top). It shall be understood that the islands be me larger or smaller than the illustrated example, for example the islands 102 may be less than 500 $\mu$m$^2$. The array is surrounded by four 90×90 $\mu$m$^2$ pads 106 in the example of FIG. 1(*a*), however larger or smaller pads 106 may be used, for example less than 150×150 $\mu$m$^2$ pads. Each island 102 is interconnected with 12 meandered nano-scale copper wires 104, of which only four are connected to the input/ output (I/O) pads. More or less than 4 meandered nanao-scale wires 104 may be used depending on the needs of the application. The microelectrode array 100 can be scaled to much smaller dimensions, enabling characterization of several test points across the surface of a single cell with a diameter of a few 1 m. In one embodiment, a high density interconnect is achieved through utilizing a commercial 45 nm CMOS Silicon on Insulator technology with eleven layers of metallizations. With multitude of interconnection layers inside each island, integration of dense circuits such as instrumentation amplifiers and signal processing circuits within each island is feasible. The integration of sensor and amplifier enables high signal-to-noise ratios and enhanced sensitivity. For example, the circuits embedded within the islands 102 or input/output pads 106 may include a computer processor (e.g., transistor-based processor), a modulator connected to the processor for wirelessly sending and receiving data to and from the computer processor via an antenna connected to the modulator.

CMOS islands are formed in a post-CMOS processing technology based on a one-step dry isotropic etching without a need for lithography. The top aluminum metallization layer in the CMOS process serves as a built-in mask to form Si islands inside an Inductively Coupled Plasma (ICP) etcher. Ultrathin (rv10 $\mu$m thick) CMOS micro-islands are then suspended using Xenon di-fluoride (XeF$_2$) gas that etches the silicon substrate underneath the array. Sidewalls are protected with a thin layer of Al$_2$O$_3$ formed by atomic layer deposition, which also provides electrical isolation. Parameters such as pressure and gas duty cycle have been optimized by taking an infrared (IR) microscope image after each etching cycle. FIGS. 2*a*-2*f* summarize the post processing steps and provides a cross sectional schematic of the islands and their interconnecting metals.

In one embodiment, the two bottom copper layers in the CMOS technology are used to form the meandered interconnects, with widths of 400 nm and thickness of 870 nm for two metal layers and a low-K dielectric layer between them. The top copper layer serves as a mask in the isotropic etching process while the bottom copper layer acts as the conductive media among sensors/circuits and I/O pads. Meandered geometries for interconnections used in this work provide excellent flexibility. On the other hand, thinning down the islands to 10 lm of dielectric/metallization layer and only 220 nm Silicon on Insulator layer reduces the stress and leads to minimal strain bending and enhanced flexibility.

In one example, the flexibility of the array was experimentally tested by applying a gentle force to the suspended array, using a computer controlled tip as illustrated in FIGS. 3(*a*) and 3(*c*). A Klocke Nanorobotics manipulator inside FEI Nova 200 dual beam FIB/SEM (Focused Ion Beam) setup was used for this purpose. While a bending radius of 560 lm was achieved, the experiment was limited by concerns about damage to the tip of the manipulator.

Polydimethylsiloxane (PDMS) was used as a soft stamp to pick up the microprobe array and transfer-print it onto a planar or concave host substrate. An in-house micromanipulator setup was used to bring the microprobe array close to the host concave substrate. As interconnections and active Si islands are monolithically integrated, they all transferred in one step. Consequently, no alignment is necessary during the transfer-printing process, which facilitates much higher yield of complex circuits in comparison to competing technologies. FIGS. 3(*b*) and 3(*d*) show a 220 lm diameter florescent microsphere coated with a thin PDMS layer (50 lm) used as a host substrate for the transfer printing procedure. Conformal wrapping of the microelectrode onto a concave hemispherical florescent surface demonstrates the flexibility of the array with extremely small bending radius. CMOS sensors exhibited no change in their DC electrical performance after transferring.

A similar experimental method was also developed to transfer cells onto the surface of a microelectrode array. FIGS. 4(*a*) and 4(*b*) illustrate optical and SEM images of a fixed mouse female germline stem cell transferred onto the microarray using a micro-tweezer. The operation mechanism of the micro-tweezer is reported elsewhere. The stem cell is fixed in a 2.0% Gultaraldehyde in 0.1 M Cacodylate buffer pH 7.4 solution prior to transferring. FIG. 4(*b*) illustrates the false color SEM picture of the microelectrode array over a mouse ova. The extreme flexibility of the microelectrode array combined with the ability to transfer-print it on a curved surface facilitates extracellular recording of cell temperature and other vital signs.

Figure 4A:
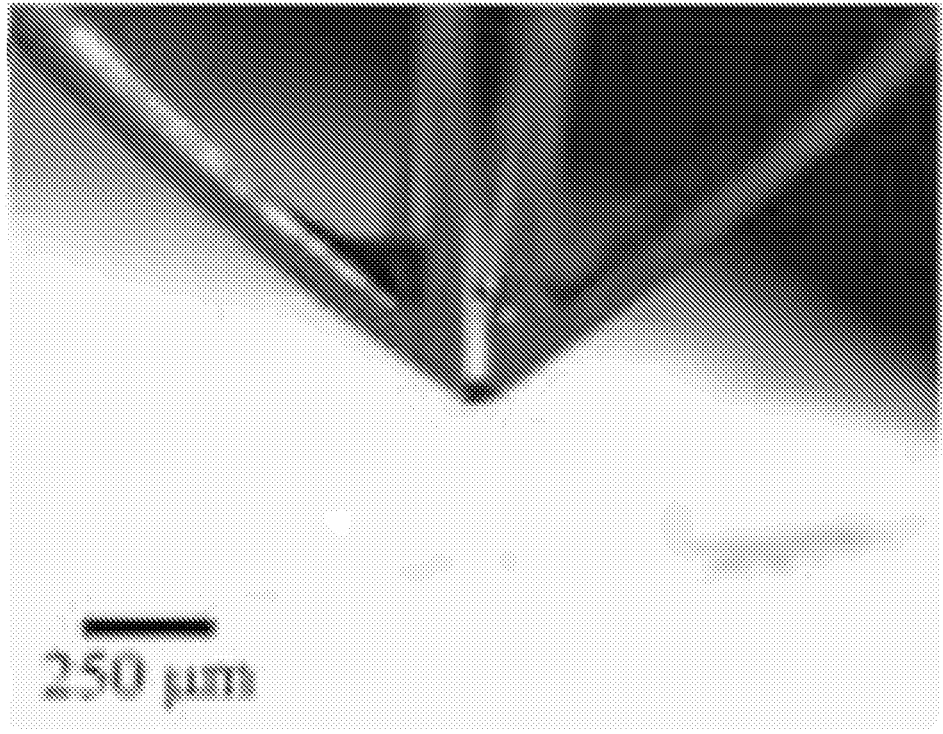
FIG. 4(a) shows an optical image illustrating the cell manipulation onto the microelectrode array using a microtweezer.
Figure 4B:
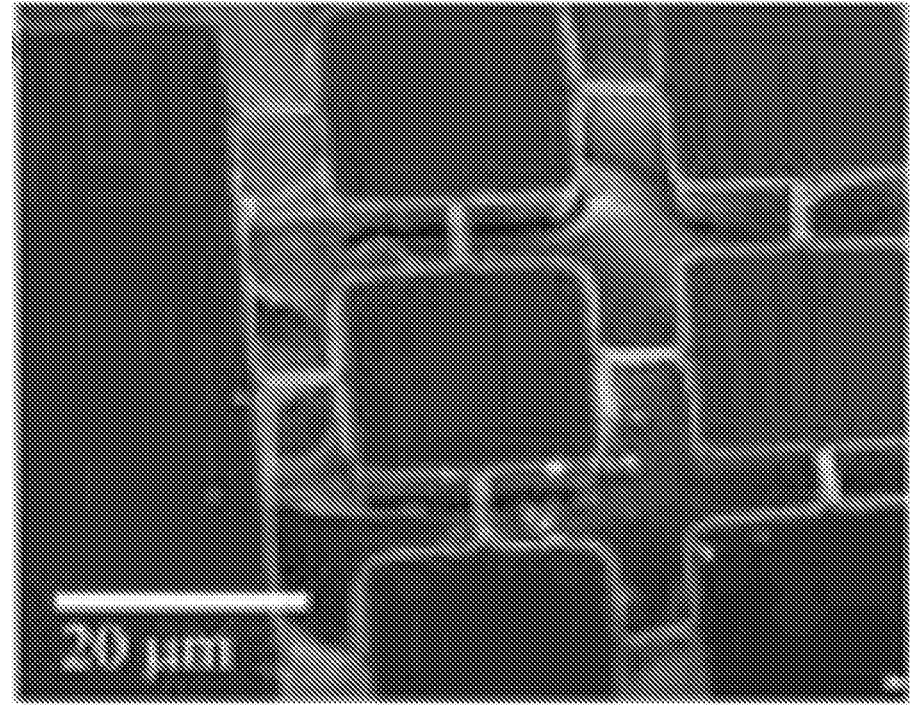
FIG. 4(b) shows an SEM image of the microelectrode array covering a mouse female germline stem cell.
Figure 4C:
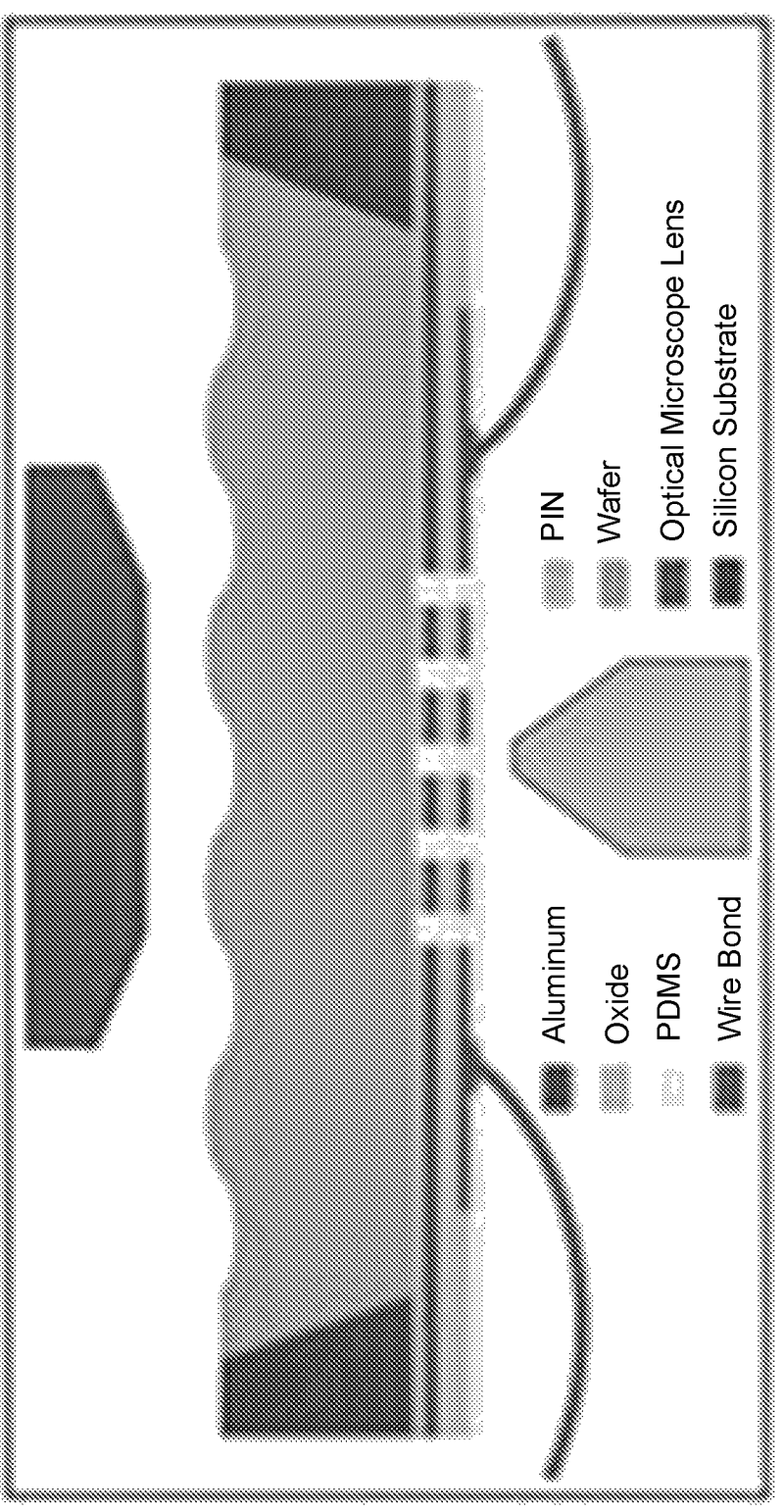
FIG. 4(c) shows a schematic of the microelectrode array under strain and in wet condition.
Figure 4D:
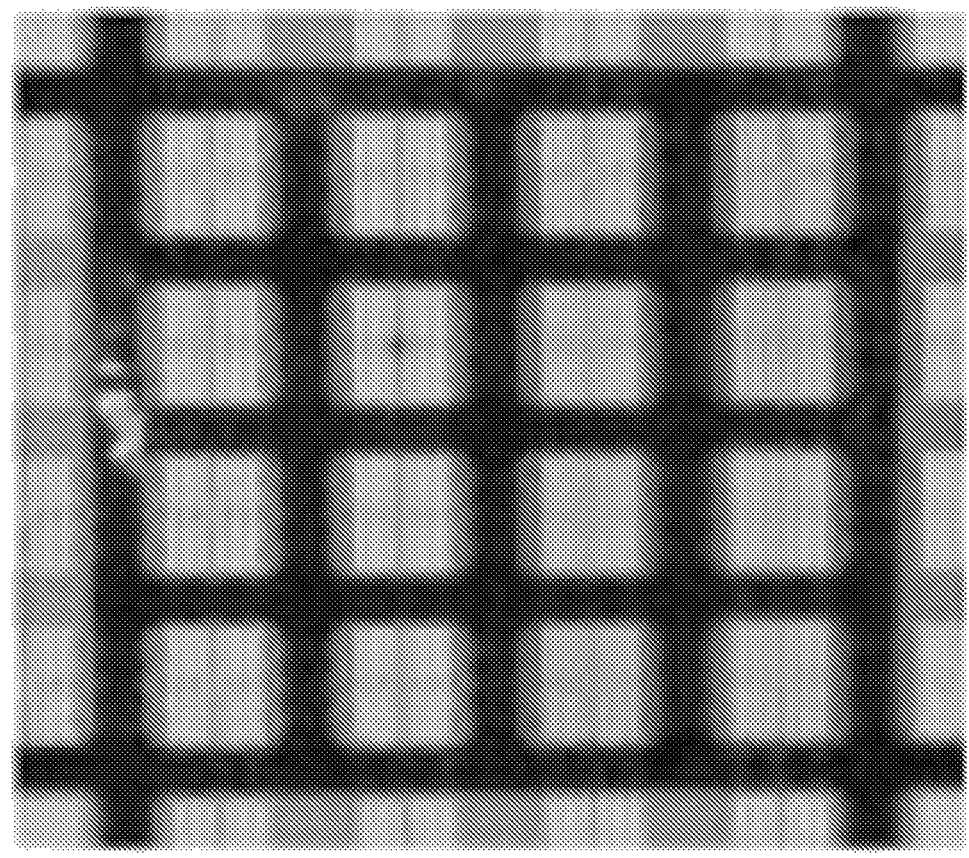
FIGS. 4(d) and 4(e) show optical microscope images of the microelectrode array before applying the strain (4(d)) and under strain (4(e)).
Figure 4E:
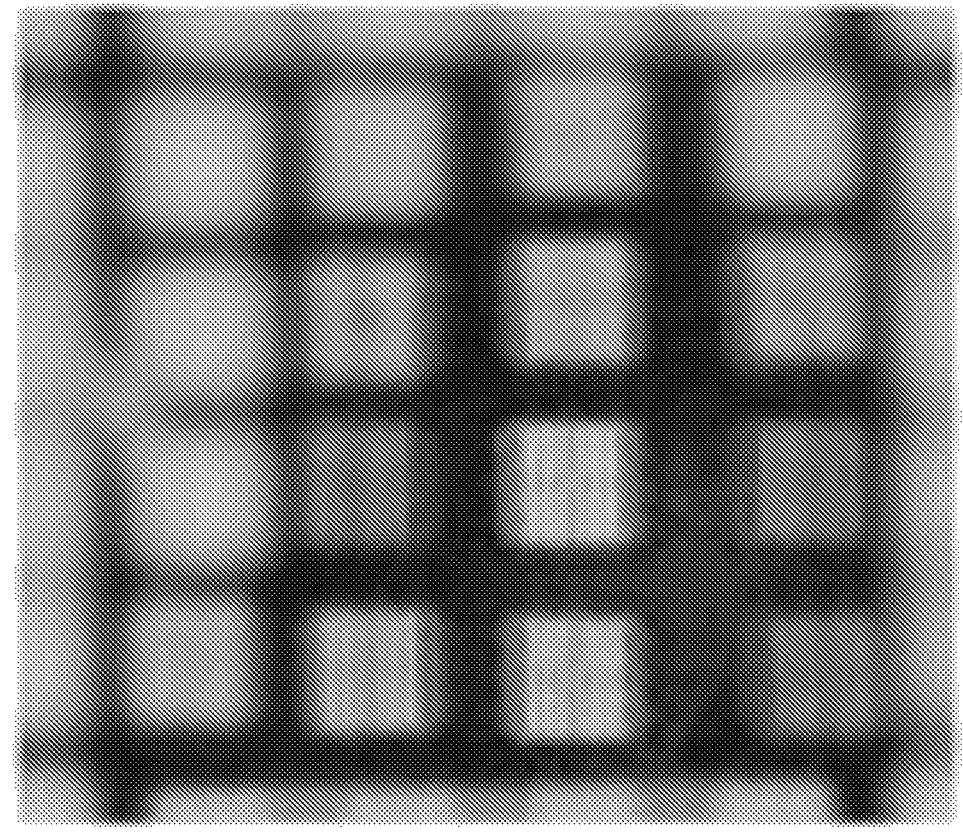
Figure 4F:
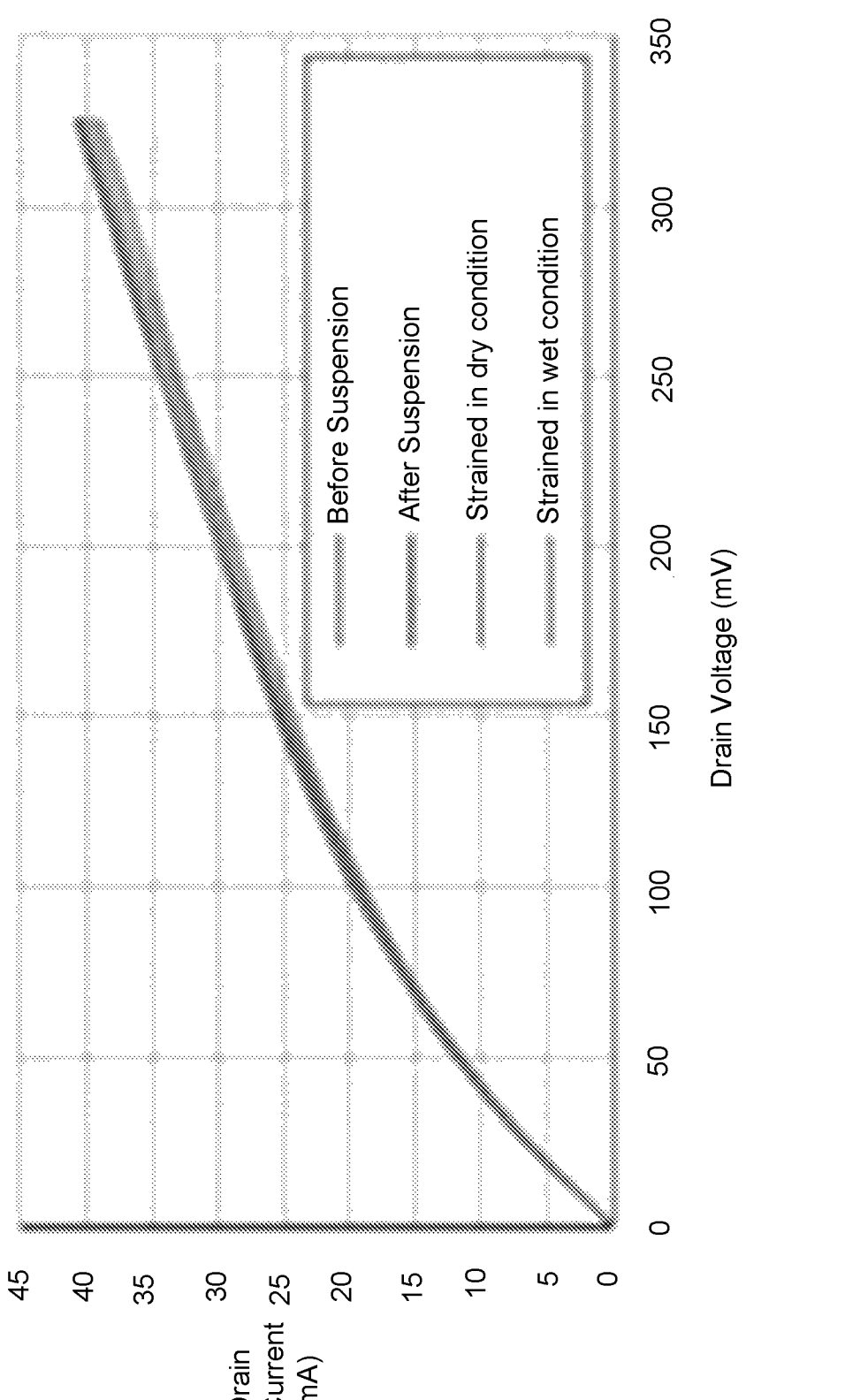
FIG. 4(f) shows an experimental measurement of the FET's Drain current vs Drain voltage under different conditions.

In order to confirm the adaptability of the microelectrode array to the real cell environment, suspended microelectrode array was characterized under mechanical strain in a wet environment. FIG. 4(c) illustrates the schematic of the setup used for this experiment. In this example, a custom made micromanipulator setup was used to move a small pin in the Z direction, in order to gently deflect the suspended microelectrode array. The entire setup was placed under an optical microscope in order to facilitated pin alignment and imaging of the experiment. FIGS. 4(d) and 4(e) illustrate the optical microscope image of the array before and after the array was deflected. FIG. 4(f) illustrates electrical measurement of the CMOS sensor in dry/wet and also in relaxed/strained conditions. Operation of the transistor is not affected by the strain of its environment.

Figure 5A:
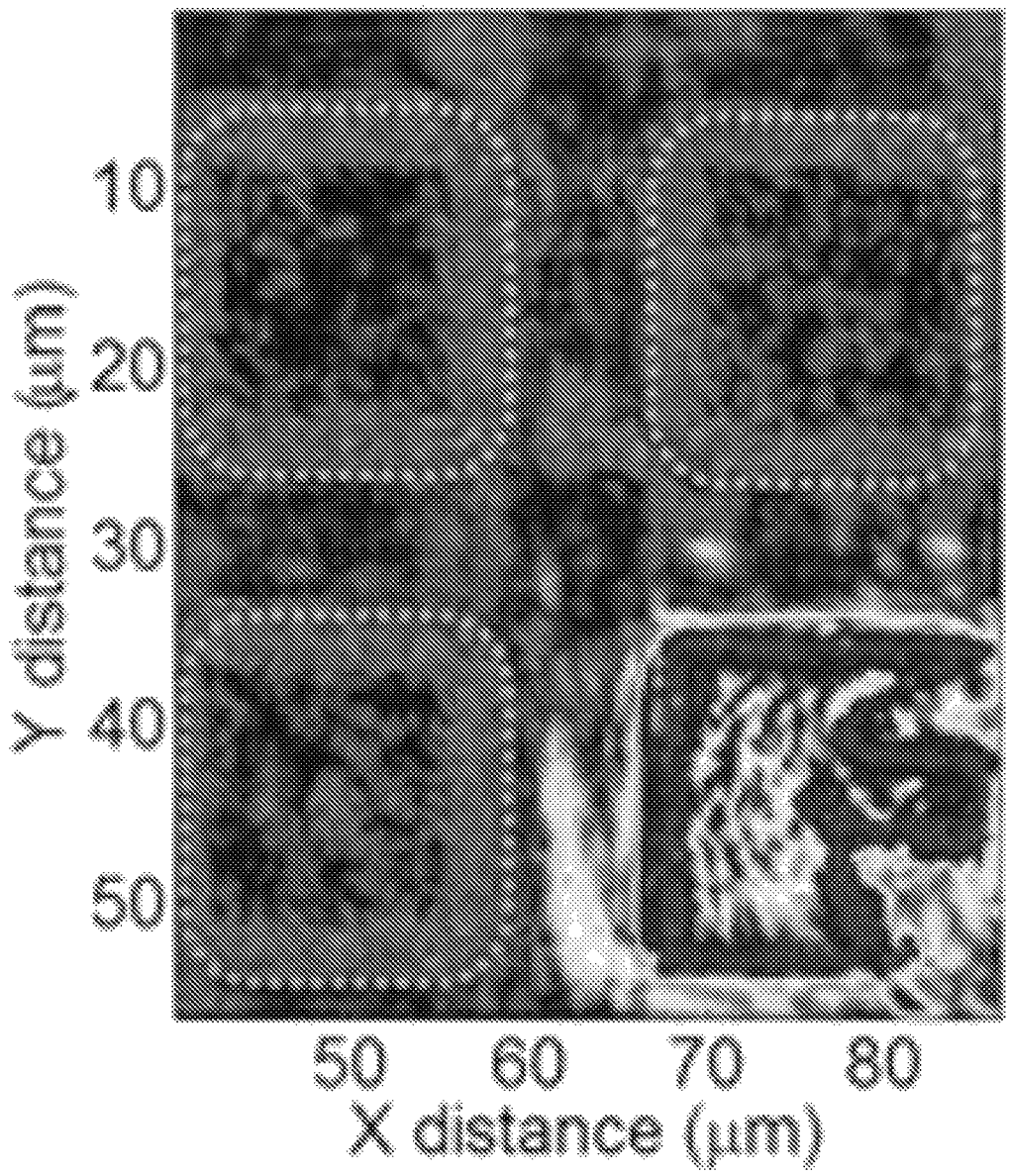
FIG. 5(a) shows a thermal micrograph of four different islands captured using non-contact thermos-reflectance technique (the bottom right island is selectively heated up to evaluate thermal leakage among islands).
Figure 5B:
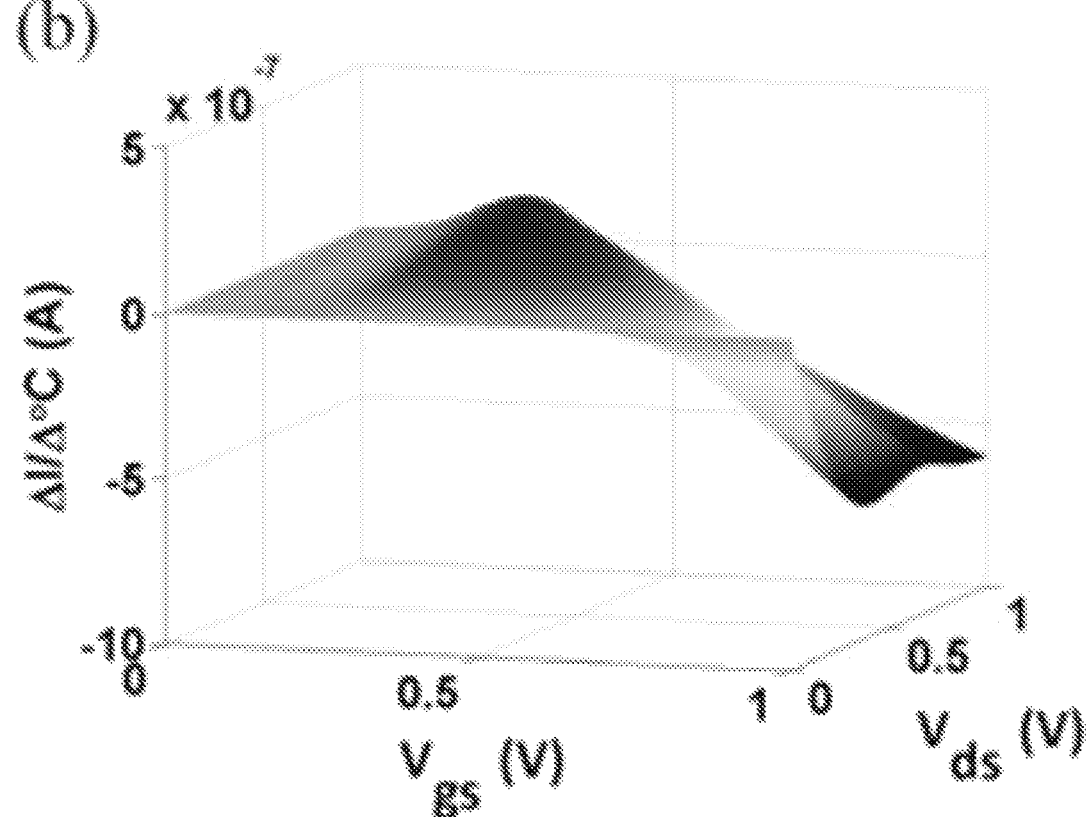
FIG. 5(b) shows a computer modeling (Cadence virtuoso simulation) of the transistor indicating the most sensitive bias operation mode with respect to temperature.

One example embodiment of the microelectrode array is in single cell thermometry. CMOS temperature sensors which have high temporal resolution (fast response). In the disclosed embodiment, the thermometer is based on buried CMOS transistors inside the islands. Note that in this experiment no live cell was used and only the thermometer was calibrated. The DC electrical characteristics of CMOS transistors change by temperature variation. The CMOS sensor was calibrated using a hotplate by monitoring the CMOS transistor drain current as the temperature of the hotplate changes in the range of 35° C.-40° C. First, the thermo-reflectance imaging microscopy was used to confirm that the array elements are thermally isolated (FIG. 5(a)). The thermal isolation facilitates reading the temperature variation across a cell (or cells) without any influence from the environment (microelectrode array thermal path). To achieve maximum temperature sensitivity, the operation of the transistor was simulated under different biasing conditions to identify the most sensitive biasing region to temperature changes as illustrated in FIG. 5(b). This enabled us to exploit the linear dependence of drain current to temperature changes. Consequently, Gate-to-Source (Vgs) and Drain-to-Source (Vds) voltages of the transistor were set to 400 mV and 300 mV, respectively, to achieve maximum temperature sensitivity at relatively small currents to avoid self-heating. FIG. 5(d) illustrates an average increase in the drain current of 370 nA/oC.

Figure 5C:
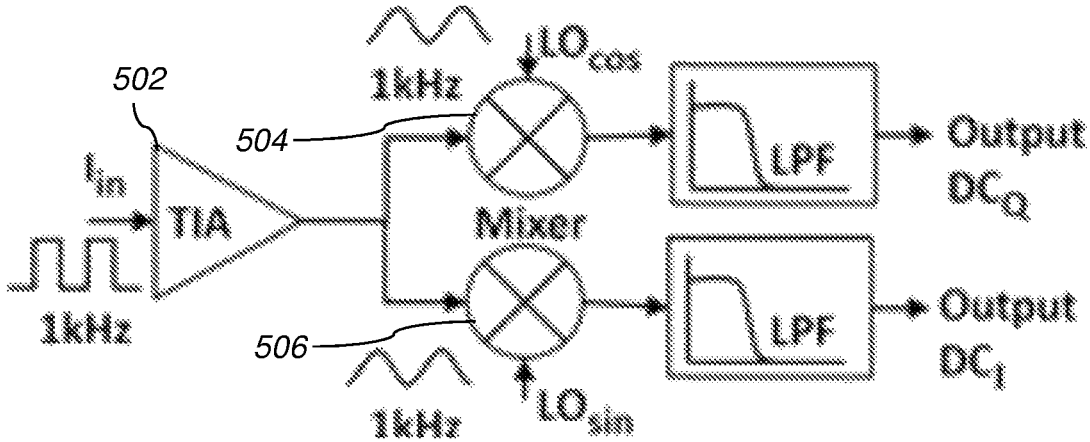
FIG. 5(c) shows a simplified schematic of the on-chip instrumentation amplifier design with an input transimpedance amplifier (TIA) and in-phase and quadrature mixers.
Figure 5D:
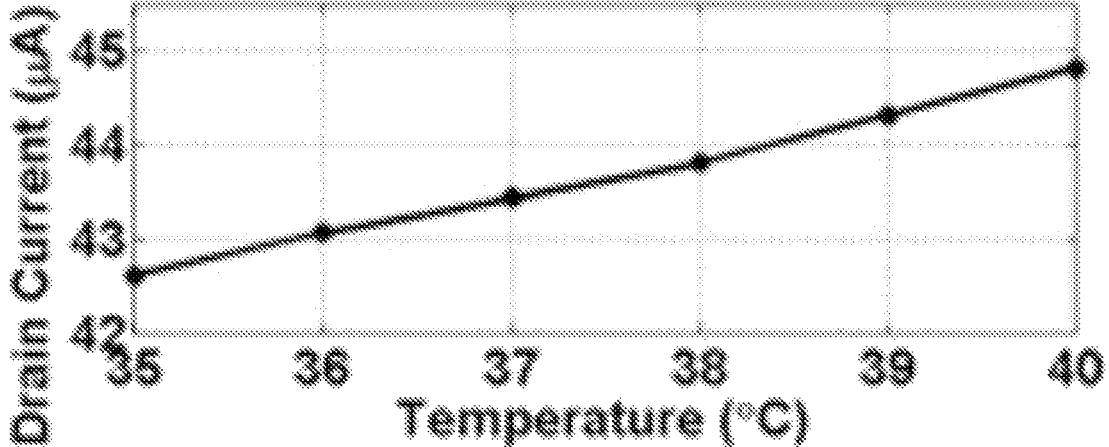
FIGS. 5(d) and 5(e) show measured temperature of the sensor in one of the islands.
Figure 5E:
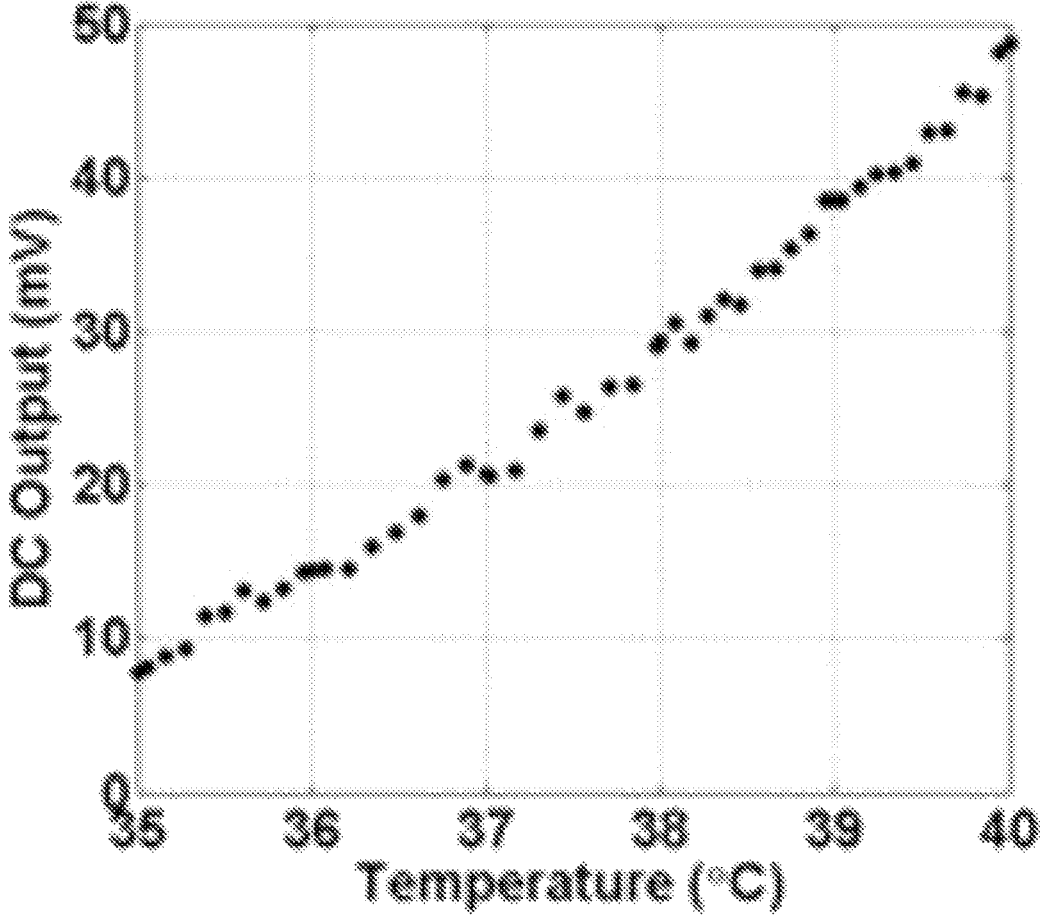

FIG. 5(c) shows a simplified schematic of the on-chip instrumentation amplifier, namely, a lock-in amplifier implemented in the 45 nm CMOS SOI process. The circuit is designed based on a Trans-impedance Amplifier (TIA) 502 and two quadrature differential phase mixers 504 and 506 connected as shown. Transistor sizes are chosen to achieve small flicker noise. FIG. 5(e) shows the output voltage of the lock-in amplifier vs temperature. With an output voltage reading standard deviation of 425 µV, a temperature sensitivity of 0.15 degrees C. is measured in this proof of concept design.

Figure 6A:
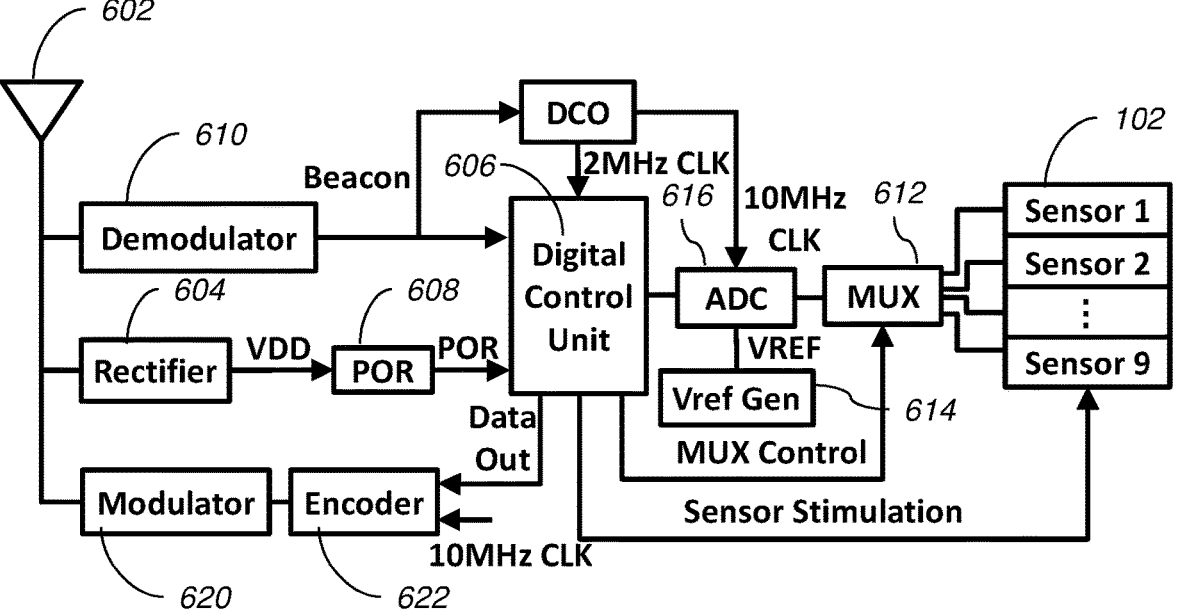
FIG. 6(a) shows a block diagram of a wireless microelectrode array circuit for biological sensing according to one embodiment.
Figure 6B:
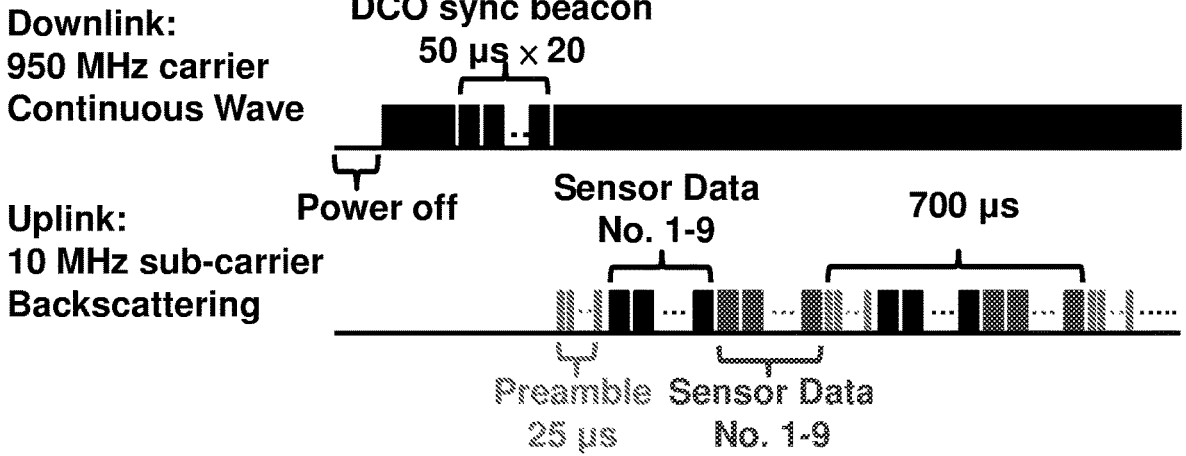
FIG. 6(b) shows a downlink and uplink timing diagrams for the system of FIG. 6(a) according to one embodiment.

FIG. 6a shows a block diagram of a further embodiment comprising an on-chip miniature antenna 602. The on-chip antenna 621 and cross-coupled NP rectifier 604 provide high power conversion and harvesting efficiency, leading to a measured dc power of 136 µW from a reader unit transmitting 1 W of power at 950 MHz and at a distance of 12 cm. Downlink and uplink timing diagrams are also shown in FIG. 6b with the uplink based on backscattering at 10 MHz offset from the power source. Power-on-reset (POR) unit 608 detects the adequate input power level to start the operation, causing a computer processor connected to and within the digital control unit 606 to send a 1 ms stimulate pulse to all 9 neural channels (islands 102). Next, the system senses the 9 recording electrodes sequentially through an analog multiplexer 612, amplifier 614, and Analog to Digital converter (ADC) 616, and transmits the information back to the reader unit. Demodulator 610 and modulator 620 and encoder 622 are also provided to wirelessly transmit the data to and from the external reader unit (not shown).

In summary, an ultraflexible thermometer array based on ultrathin CMOS islands interconnected and hold together with meandered Cu metals is disclosed herein. Unlike prior art extracellular recording techniques that are performed by electrodes from a distance of about 100 µm from the cell, the presently disclosed flexible microelectrode array conforms to the cell, facilitating an unprecedented access to "cellular information". Monolithic nature of silicon membranes and their meandered interconnections bypass the yield and signal integrity limitations of existing transfer-printed circuits. The presently disclosed flexible microelectrode array enables simultaneous measurements at several sites, with direct contact to the cell surface. The use of a standard CMOS process and a simple post-processing technology that does not use any lithography combined with a one-step transfer-printing method has facilitated an important milestone for future flexible and stretchable electronics. The presently disclosed system can be used for flexible multi-functional sensing systems and may find a variety of applications including precision single-cell characterization, sensory skins, and smart wound therapy. These applications are emerged from conformal coverage of microcurvatures combined with highly reliable and flexible complex integrated circuits achieved by the presently disclosed microelectrode array.

Those skilled in the art will recognize that numerous modifications can be made to the specific implementations described above. The implementations should not be limited to the particular limitations described. Other implementations may be possible.

The invention claimed is:

1. A method of forming a biological sensing system, comprising:
   providing a CMOS chip, the chip comprising an array of first metal regions in a top layer of the chip and a plurality of second metal regions, the second metal regions having a meandering shape interconnecting areas below the first metal regions;
   applying an anisotropic dry etching using Inductively Coupled Plasma (ICP), wherein the first metal regions provide masking to form an array of islands in the chip;
   depositing a metal oxide layer on sidewalls of the islands to form a protective barrier;
   further etching regions between the islands to form an etched region under the interior islands of the array, leaving only the second metal regions mechanically interconnecting the interior islands.

2. The method of claim 1, further comprising transfer-printing the array onto a substrate.

3. The method of claim 2, wherein the transfer-printing is performed using polydimethylsiloxane as a soft stamp to retrieve the array from the chip.

4. The method of claim 1, wherein the second metal regions mechanically and electrically interconnect the interior islands.

* * * * *